United States Patent [19]
Murphy et al.

[11] Patent Number: 5,972,657
[45] Date of Patent: Oct. 26, 1999

[54] **GENE ENCODING OUTER MEMBRANE PROTEIN B1 OF *MORAXELLA CATARRHALIS***

[75] Inventors: Timothy F. Murphy, Amherst; Sanjay Sethi, Williamsville, both of N.Y.

[73] Assignee: The Research Foundation of State University of New York, Amherst, N.Y.

[21] Appl. No.: 08/949,941

[22] Filed: Oct. 14, 1997

[51] Int. Cl.[6] .............................. C12P 21/06; C12P 21/04; C12N 15/00; C07H 21/04
[52] U.S. Cl. .................... 435/69.3; 435/71.1; 435/320.1; 435/325; 536/23.7
[58] Field of Search .................................. 435/69.3, 71.1, 435/320.1, 325; 536/23.7

[56] References Cited

FOREIGN PATENT DOCUMENTS

97/32980  9/1997  WIPO.

OTHER PUBLICATIONS

Sethi, et al., "Serum Antibodies to Outer Membrane Proteins of *Moraxella catarrhalis* in Patients with Bronchiectasis: Identification of OMP B1 as an Important Antigen," 1995, Infection and Immunity, vol. 63. pp. 1516–1520.

Campagnari, et al., "Outer Membrane Protein B1, an Iron–Repressible Protein Conserved in the Outer Membrane of *Moraxella catarrhalis*, Binds Human Transferrin", Infection abd Immunity, 1996, vol. 64, No. 9, pp. 3920–3924.

*Primary Examiner*—Anthony C. Caputa
*Assistant Examiner*—Mark Navarro
*Attorney, Agent, or Firm*—Hodgson, Russ, Andrews, Woods & Goodyear, LLP

[57] ABSTRACT

Nucleotide sequences, derived from *Moraxella catarrhalis*, which encode one or more epitopes of outer membrane protein B1 are disclosed. Recombinant B1 protein or B1 peptides may be produce by culturing in a medium a host cell genetically engineered to contain and express a nucleotide sequence according to the present invention, and recovering the recombinant protein or peptide from the cultured host cell or culture medium. The nucleotide sequence of the present invention can also be used in molecular diagnostic assays for detecting *M. catarrhalis* genetic material, and in antigenic compositions for producing B1-specific amino acids.

18 Claims, No Drawings

GENE ENCODING OUTER MEMBRANE PROTEIN B1 OF *MORAXELLA CATARRHALIS*

This invention was made with government support under grant AI2830409 awarded by the National Institutes of Health, and support by the Department of Veteran Affairs. The government has certain rights in the invention.

FIELD OF INVENTION

The present invention relates a gene encoding a protein associated with the outer membrane of *Moraxella catarrhalis*. More particularly, the invention is directed to the isolation and purification of a gene encoding outer membrane protein B1 of *M. catarrhalis*, compositions comprising the gene encoding B1 protein or portions of the gene, and uses thereof. Related thereto, disclosed are DNA sequences encoding B1 protein, vectors useful in directing the expression of B1 protein or peptides thereof, and host cells transformed with such vectors. The nucleotide sequences disclosed provide for the synthesis of corresponding oligonucleotides which can be used as reagents in diagnostic assays directed to the detection of *M. catarrhalis* genetic material.

BACKGROUND OF THE INVENTION

*Moraxella catarrhalis* is an important human respiratory tract pathogen. *M. catarrhalis* is the third most common cause of otitis media in infants and children, after *Streptococcus pneumoniae* and nontypeable *Haemophilus influenzae*, as documented in studies in which tympanocentesis has been used to establish the etiologic agent (Murphy, 1989, *Pediatr. Infect. Dis. J*. 8:S75–S77). *M. catarrhalis* is a common cause of sinusitis and conjunctivitis in both children and adults (See for example, Bluestone, 1986, *Drugs* 31:S132–S141; Brorson et al., 1976, *Scand. J. Infect. Dis.* 8:151–155; and Romberger et al., 1987, *South. Med. J.* 80:926–928); and is an important cause of lower respiratory tract infections in adults with chronic bronchitis and chronic obstructive pulmonary disease (Murphy et al., 1992, *Am. Rev. Respir. Dis*. 146:1067–1083; Catlin, 1990, *Clin. Microbiol. Rev*. 3:293–320). Additionally, *M. catarrhalis* can cause pneumonia, endocarditis, septicemia, and meningitis in immunocompromised hosts (Cocchi et al., 1968, *Acta Paediatr. Scand*. 57:451–3; Douer et al., 1977, *Ann. Intern. Med.* 86:116–119; McNeely et al., 1976, *Am. Rev. Respir. Dis.* 114:399–402).

Since recurrent otitis media is associated with substantial morbidity, and the attendant health care costs, there is interest in developing strategies for identifying and preventing these infections. One such approach is the development of vaccines for preventing bacterial otitis media. Besides infants and children benefitting from a vaccine to prevent otitis media caused by *M. catarrhalis*, adults with chronic obstructive pulmonary disease, and immunocompromised children and adults would benefit from a vaccine to prevent infections caused by *M. catarrhalis*. Outer membrane proteins are being investigated as antigens having utility in diagnosing and vaccinating against disease caused by bacterial pathogens, such as *M. catarrhalis*.

In an original typing scheme, eight major outer membrane proteins, designated by the letters A–H, were identified (Murphy et al., 1989, *Microbial Pathogen.* 6:159–174; Bartos et al., 1988, *J. Infect. Dis.* 158: 761–765). Further characterization of the outer membrane proteins of *M. catarrhalis* have added to this typing scheme. A protein having an apparent molecular mass of approximately 80 to 81 kilodaltons (kDa), as determined by sodium dodecyl polyacrylamide gel electrophoresis (SDS-PAGE), has been described previously ("CopB protein": Helminen et al., 1993, *J. Inf. Dis.* 168:1194–201; "OMP B2 protein": Sethi et al., 1995, *Infect. Immun.*, 63:1516–1520). CopB protein has been characterized as a surface-exposed, antigenically conserved protein that is a target for antibodies that enhance pulmonary clearance of *M. catarrhalis* in an experimental model of infection (Helminen et al., 1993, *Infect. Immun.* 61:2003–2010). Further, CopB may be involved in the serum resistance of *M. catarrhalis* in an infected host (Helminen et al., 1993, *J. Inf. Dis.* 168:1194–201).

Another outer membrane protein, B1, has recently been described. B1 protein was shown to be expressed in detectable amounts in the outer membrane of *M. catarrhalis* under iron-limiting conditions, i.e., expressed when the organism is growing in an iron-limited environment (Campagnari et al., 1994, *Infect. Immun.* 62:4909–4914). However, when the organism is grown in an iron-rich environment, the expression of the B1 protein becomes repressed. The B1 protein, having an apparent molecular mass of approximately 81 to 84 kilodaltons (kDa) as determined by SDS-PAGE, has been demonstrated to be distinct from the CopB (OMP B2) protein by differences in migration pattern in polyacrylamide gels, by antibody reactivity, and by expression in iron-limiting conditions (Campagnari et al., 1994, supra; and Campagnari et al., 1996, *Infect. Immun.* 64:3920–4). Further characterization of the B1 protein has demonstrated that it is a transferrin binding protein (Campagnari et al., 1996, supra). Several species of bacteria (e.g., Neisseria, Haemophilus, and Actinobacillus) have exhibited the ability to bind transferrin, and appear to use transferrin as a major iron source. For bacteria in general, there appears to be a correlation between virulence, and the ability to scavenge iron from the host.

Additional studies show that OMP B1 contains epitopes exposed at the surface of the bacterium expressing it, and that these surface-exposed epitopes are important antigens for the human humoral response to *M. catarrhalis* infection (Sethi et al., 1995, *Infect. Immun*. 63:1516–1520). More particularly, in several bronchiectatic patients tested, the major target of serum IgG against *M. catarrhalis* was B1 protein; and this observed immune response was consistently of high titer. Subsequently, it has been shown that patients with chronic obstructive pulmonary disease who have exacerbations due to *M. catarrhalis*, develop serum IgG and sputum IgA antibodies to B1 protein. Also children with otitis media have abundant antibodies to B1 protein in their convalescent sera (Campagnari et al., 1996 supra).

Properties of the B1 protein indicate that the gene encoding the B1 protein has utility in the diagnosis of and vaccination against diseases caused by bacterial pathogens, such as *M. catarrhalis*, that produce B1 protein or surface-exposed epitopes cross-reactive with B1 protein epitopes. Thus, it would be advantageous to provide for the identification, isolation, and purification of the gene encoding B1 protein for use as diagnostic reagents, for antigenic/immunogenic preparations such as vaccines, and for recombinant production of B1 protein.

SUMMARY OF THE INVENTION

In accordance with one object of the present invention, there is provided the identification, isolation and purification of a gene encoding outer membrane protein B1 from a bacterial strain that produces B1 protein, e.g. *Moraxella catarrhalis*.

Another object of the present invention is to provide novel DNA sequences and vectors including plasmid DNA, and viral DNA such as human viruses, animal viruses, insect viruses, or bacteriophages which can be used to direct the expression of the B1 protein or peptides thereof, in appropriate host cells from which the expressed protein or peptides may be purified.

A further object of the present invention is to provide methods for molecular cloning of the gene encoding B1 protein, and to provide compositions comprising oligonucleotides within the gene sequence encoding B1 protein. The nucleic acid sequences of the present invention can be used in molecular diagnostic assays for *M. catarrhalis* genetic material through nucleic acid hybridization, and including the synthesis of B1 sequence-specific oligonucleotides for use as primers and/or probes in amplifying, and detecting amplified, nucleic acids.

Yet another object of the present invention is to provide a gene encoding B1 protein, or one or more gene fragments encoding B1 peptides, operatively linked to one or more regulatory elements, which can be introduced directly into humans to express B1 protein or B1 peptides, to elicit an immune response.

These objects and further features and advantages of the invention will be better understood from the description of the preferred embodiments which are offered for purposes of illustration, and not limitation.

DETAILED DESCRIPTION OF THE INVENTION

Definitions

By the terms "OMP B1", and "B1 protein" are meant, for the purposes of the specification and claims, to refer to a protein having the following distinguishing and functional characteristics:

(a) the protein is substantially expressed by a bacterial strain that produces B1 protein, e.g., *M. catarrhalis*, and is detectable in the outer membrane of the bacterial strain, under iron-limiting conditions, i.e., when the organism is growing in an iron-limited environment;

(b) expression of the protein appears to become repressed when the bacterial strain is grown in an iron-rich environment;

(c) the protein has an apparent molecular mass of approximately 81 to 84 kDa as determined by SDS-PAGE;

(d) the protein, in its native conformation in the outer membrane, contains surface-exposed epitopes; and (e) the protein binds human transferrin, particularly iron-saturated transferrin.

Additionally, the amino acid sequence of the protein is substantially that shown in SEQ ID NO:2 ("substantially" encompasses conservative substitutions).

By the term "individual" is meant, for the purposes of the specification and claims to refer to any mammal, especially humans.

By the term "operably linked" is meant, for the purposes of the specification and claims to refer to the chemical fusion (restriction with subsequent ligation) or synthesis of heterologous DNA with a nucleotide sequence that encodes B1 protein, or a peptide thereof, such that the resultant recombinant DNA molecule is formed in a proper orientation and reading frame for the nucleotide sequence to be transcribed into functional RNA. In the construction of the recombinant DNA molecule, it is generally preferred to position a promoter at a distance upstream from the initial codon of the nucleotide sequence that is approximately the same as the distance in its natural setting (e.g., as in the *M. catarrhalis* genome). However, as known in the art, some variation in the distance can be accommodated without loss of promoter function. Likewise, it is generally preferred to position an enhancer element at a distance upstream from the promoter, or incorporated into the promoter sequences as a promoter element, or located between the promoter and the DNA molecule to be expressed. However, as known in the art, some variation in the placement can be accommodated without loss of the enhancer element's function.

By the term "expression vector" is meant, for the purposes of the specification and claims to refer to a DNA molecule which is operably linked to a nucleotide sequence that encodes B1 protein, or a peptide thereof, such that the production of the protein or peptide is effected in a suitable host. The vector may include, but is not limited to, a plasmid, phage, viral vectors, viral-like vectors, or a potential genomic insert.

By the terms "variant sequence" are meant, in reference to the gene encoding B1 protein and for the purposes of the specification and claims to refer to a nucleotide sequence that shares substantial identity (an identity of greater than about 85%, including taking third base degeneracy into account) with the gene encoding B1 protein. Such a sequence comparison can be performed using existing software known to those skilled in the art. Variants can be natural variants (e.g., variation in the gene encoding B1 protein seen between different strains of *M. catarrhalis*) or variants produced by synthetic or mutagenic means for modifying the disclosed nucleotide sequences. With respect to such variations, and as appreciated by those skilled in the art, because of third base degeneracy, almost every amino acid can be represented by more than one triplet codon in a coding nucleotide sequence. Thus, a variant sequence be modified slightly in sequence (e.g., substitution of a nucleotide in a triplet codon), and yet still encode its respective gene product of the same amino acid sequence as encoded by the disclosed nucleotide sequences. Further, variant sequences may have minor base pair changes which may result in variation (conservative substitution) in the amino acid sequence encoded. Such conservative substitutions are not expected to substantially alter the biologic activity of the gene product. A conservative substitution or modification of one or more amino acids are such that the tertiary configuration of the protein is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. A variant sequence may contain a modification, being defined functionally as resulting in a deletion or addition or substitution of one or more amino acids which does not impart a substantial change in the B1 protein that it encodes; i.e., the encoded B1 protein substantially retains the activity of binding transferrin. Methods for synthetically producing such variant sequences are known to those skilled in the art (see, e.g. U.S. Pat. Nos. 5,403,737 and 5,275,945).

By the terms "consisting essentially of" a nucleotide sequence are meant, for the purposes of the specification and claims to refer to the base pair changes (substitution) in the nucleotide sequence such as a change in the third base of a triplet codon (third base degeneracy) or a change resulting in the encoding of a conservative substitution in the amino acid sequence encoded, or a variant sequence as defined above.

By the terms "% similarity" are meant, for the purposes of the specification and claims to refer to the percent of amino acids that are not identical, but similar (amino acids having substantially the same charge, size, hydrophilicity, and/or aromaticity) between two amino acid sequences as determined by sequence comparisons performed using algorithms known to those skilled in the art.

By the terms "% identity" used in conjunction with protein or peptide are meant, for the purposes of the specification and claims to refer to the percent of amino acid positions that are identical between two amino acid sequences as determined by sequence comparisons performed using algorithms known to those skilled in the art.

By the terms "% identity" used in conjunction with a nucleic acid molecule are meant, for the purposes of the specification and claims to refer to the percent of nucleotide base positions that are identical between two nucleic acid molecules as determined by sequence comparisons performed using algorithms known to those skilled in the art.

The present invention is directed to a gene encoding a bacterial outer membrane protein of *M. catarrhalis* wherein the protein has been designated "B1". One role of this protein to the growth and survival of *M. catarrhalis* relies on the binding specificities of the B1 protein. It is well established that iron is a critical element which is essential for the growth of many different microbial pathogens. Most of the iron present in the human body is intracellular in the ferrous form as hemoglobin, heme, ferritin, and hemosiderin. Most extracellular iron is complexed to the high affinity iron-binding glycoproteins transferrin and lactoferrin. Thus, with the virtual absence of free iron available in the body because of the presence of various iron-binding compounds, many microbial pathogens in humans have had to develop highly specific mechanisms by which to obtain the necessary iron for survival in vivo. These mechanisms include, but are not limited to the production of hemolysins to free intracellular iron from heme and hemoglobin; the secretion of siderophores, high affinity iron chelators which compete for iron in the microenvironment and which are then internalized by the microbial pathogen; and the expression of specific OMPs in response to iron limitation, wherein the OMPs having affinity for iron-binding compounds.

The unexpected finding that the B1 protein binds iron-saturated transferrin provides evidence that the B1 protein is involved in one of the mechanisms by which *M. catarrhalis* obtains iron from the iron-binding compound human transferrin. It has recently been demonstrated that *M. catarrhalis* can utilize human transferrin as the sole source of iron for in vitro growth (Campagnari et al., 1994, *Infect. Immun.* 62:4909–4914, herein incorporated by reference). Because B1 protein appears to play an important role for *M. catarrhalis* survival in vivo, this finding is one factor in considering using the gene encoding B1 protein as an immunogen in a vaccine against disease caused by *M. catarrhalis*. For example, OMPs that function as transferrin-binding proteins, have been demonstrated to be important in the pathogenesis of infections caused by pathogenic bacteria *Neisseria meningitidis* and *N. gonorrhoeae* (Criado et al., 1993, *Res. Microbiol.* 144:77–82; Litwin et al., 1993, *Clin. Microbiol. Rev.* 6:137–149). Antibodies induced to a transferrin binding protein may function to inhibit bacterial growth such as by bactericidal activity, and/or inhibiting transferrin binding to the transferrin binding protein thereby iron-starving the bacteria (Lissolo et al., 1995, *Infect. Immun.* 63:884–90). Thus, isolated and purified gene encoding B1 protein, or a gene fragment encoding a portion of the B1 protein (e.g., the transferrin binding domain), may be used as immunogens in various vaccine formulations in the prevention of otitis media, sinusitis, conjunctivitis, and lower respiratory tract infections caused by *M. catarrhalis*. Also, the isolated and purified gene encoding B1 protein, or a gene fragment encoding antigenic portions of E1 protein, may be used to produce B1 protein or B1 peptide for use as an antigen for diagnostic immunoassays or for generating *M. catarrhalis*-specific antisera of diagnostic value.

The present invention further provides the nucleotide sequence of the gene encoding B1 protein, as well as the amino acid sequence deduced from the isolated gene. As indicated by a nucleotide sequence of the present invention (SEQ ID NO:1), the gene encoding B1 protein reveals that the predicted amino acid sequence of the mature B1 protein has a calculated molecular mass of about 74,600 daltons; and B1 protein comprises an amino acid sequence of SEQ ID NO:2. According to one embodiment of the present invention, using recombinant DNA techniques the gene encoding B1 protein, or gene fragments encoding one or more B1 peptides having at least one antigenic epitope, is incorporated into an expression vector, and the recombinant vector is introduced into an appropriate host cell thereby directing the expression of these sequences in that particular host cell. The expression system, comprising the recombinant vector introduced into the host cell, can be used (a) to produce B1 protein, or B1 peptides, which can be purified for use as antigenic formulations comprising vaccine formulations or for generating *M. catarrhalis*-specific antisera of therapeutic and/or diagnostic value; (b) to produce B1 protein or B1 peptides to be used as an antigen for diagnostic immunoassays; c) or if the recombinant expression vector is a live virus such as vaccinia virus, the vector itself may be used as a live or inactivated vaccine preparation to be introduced into the host's cells for expression of B1 protein or antigenic B1 peptides; d) or if the recombinant expression vector is introduced into live attenuated bacterial cells which are used to express B1 protein, or B1 peptides to vaccinate individuals; e) or introduced directly into an individual to immunize against the encoded and expressed B1 protein or B1 peptide.

For purposes of the description, the methods and compounds of the present invention will be illustrated in the following examples.

EXAMPLE 1

This example illustrates the molecular cloning and sequencing of the gene encoding B1 protein, and vectors expressing B1-specific epitopes (epitopes comprising the B1 protein, or peptides thereof). The strategy used was to isolate genomic DNA from *M. catarrhalis*, cleave the isolated DNA into fragments, construct a genomic library comprising insertion of the fragments into an expression vector, introduce the recombinant vectors into the appropriate host cell, and immunoscreen the library for host cell clones containing the gene encoding B1-specific epitopes by immunoscreening the library using human polyclonal antisera having binding specificity for the B1 protein.

*Moraxella catarrhalis* strain FM2, isolated from the sputum of a patient with bronchiectasis, was used as the source of bacterial genomic DNA. *M. catarrhalis* was grown on chocolate agar plates at 37° C. in 5% $CO_2$ or in brain heart infusion broth. *Escherichia coli (E. coli)* XL-1 Blue was used as the host strain for the bacteriophage (lambda TriplEx; Clontech Labs) genomic library. *E. coli* strain BM25.8 was used as the host strain for subcloning. A lambda library was constructed with genomic DNA of *M. catarrhalis* FM2 using previously described methods (Ausubel et al., 1989, Current Protocols in Molecular Biology, published by John Wiley and Sons). Genomic DNA of *M. catarrhalis* strain FM2 was purified using detergent extraction, and proteinase treatment. The purified genomic DNA (500 μg) was then partially digested with restriction enzyme Apo1 (6.5 units) to generate fragments varying in size. The DNA fragments were separated by sucrose gradient centrifugation on a 10% to 40% sucrose gradient. Fractions containing fragments of approximately 4 to 8 kilobases (kb) in size were collected, and concentrated by ethanol precipitation. The DNA was subsequently ligated to λTriplEx phage arms (predigested with EcoRI) with T4 DNA ligase and then packaged into phage. A genomic library of $2\times10^8$ pfu/ml titer was obtained (pfu=plaque forming units).

Polyclonal anti-B1 antisera, obtained from a patient with bronchiectasis was determined to recognize B1 protein as the only *M. catarrhalis* strain FM2 antigen, at a dilution of 1:5000 in Western blot assays. Cross-reacting antibodies to *E. coli* were adsorbed from the antisera. Briefly, the antisera (30 μl) was mixed with 1% nonfat dried milk (970 μl) in buffer (phosphate buffered saline with detergent; PBS with 0.05% Tween™) and incubated with *E. coli* (harvested from an overnight culture) with agitation for 4 hours at room temperature. The non-cross-reactive antibodies (including the B1-specific antibodies) were separated from bacteria by centrifugation. This adsorbed antisera was diluted to a final concentration of 1:5000, and used to probe the λ library. Dilutions of the unamplified library, titrated to yield approximately 1000 pfu per culture plate, were incubated for 20 minutes with *E. coli* XL1-Blue in 10 mM $MgSO_4$ at 37° C. Three ml of top agar was added, the mixture was spread on culture plates of LB agar plus carbenicillin, and incubated for 4 hours at 42° C. until the plaques were visible. Nitrocellulose filters were soaked in 10 mM IPTG (isopropyl-β-D-thiogalactopyranoside), and allowed to air dry until damp. The filters were then placed onto the top agar, and the plates were then incubated at 37° C. for 4 hours. The plates were then cooled at 4° C. for 30 minutes, the position of the filters relative to the plates were marked by ink, and then the filters were removed. The filters were washed with buffer, and the filters were then blocked in buffer containing 1% nonfat dried milk for 1 hour. The blocked filters were incubated with the adsorbed serum (1:5000 dilution) over-night at room temperature. The filters were then washed with buffer, and incubated in peroxidase-labeled goat anti-human IgG (diluted 1:2000 in buffer) for 1 hour. After washing, the filters were developed by adding calorimetric substrate. Twenty immunoreactive plaques were obtained in the first round screening of 10,000 plaques. Plaques which appeared immunoreactive by this method were purified, and the screening procedure was repeated. Four purified plaques, repeatedly immunoreactive with the anti-B1-antisera, were selected for further analysis.

The four immunoreactive plaques, and a negative control (one plaque not immunoreactive with the anti-B1 antisera) were transformed to plasmid clones by cre-lox mediated conversion according to the manufacturer's conversion protocol (Clontech Labs). *E. coli* host strain BM25.8 was grown in LB broth with 10 mM $MgSO_4$ overnight at 31° C. Magnesium chloride was added to a final concentration of 10 mM to the overnight culture. Well isolated positive phage plaques were individually picked, and eluted overnight in dilution buffer. One hundred μl of the eluted phage was incubated with 200 μl of the *E. coli* host strain suspension for 30 minutes at 31° C. Four hundred μl of LB broth was added, and the incubation was continued for an additional 1 hour. Ten μl of the cell suspension was removed and spread on a plate containing LB agar with carbenicillin (60 μg/ml), and incubated overnight at 37° C. Several isolated colonies were picked, and grown on plates containing LB agar with carbenicillin, IPTG, and X-gal (5-bromo-4-chloro-3-indolyl-β-D-galactoside). A loopful of the culture was suspended in SDS-PAGE sample buffer, boiled for 10 minutes, and loaded on an 11% SDS polyacrylamide gel. After electrophoresis, the proteins were transferred to nitrocellulose membranes, and screened for immunoreactivity with an anti-B1 monoclonal antibody. The Western blot showed that clone 6A7 contained an immunoreactive band of the same apparent molecular weight as OMP B1 of *M. catarrhalis* strain FM2.

DNA from one positive clone, 6A7, was purified using a commercial maxiprep purification kit according to the manufacturer's instructions (Promega Corp.). Clone 6A7 contained a plasmid having a 4.8 kb insert. Using automated microsequencing, this insert was sequenced in its entirety in both directions. An open reading frame of 2136 base pairs was identified (SEQ ID NO:1). The deduced amino acid sequence of the encoded protein is 712 amino acids in length (SEQ ID NO:2), with a leader sequence comprising amino acids 1 to 21 of SEQ ID NO:2. Thus, a nucleotide sequence comprising nucleotide 64 to nucleotide 2136 of SEQ ID NO:1 encodes the amino acid sequence of the mature B1 protein (comprising amino acids 22 to 712). The nucleotide sequence (SEQ ID NO:1) encoding the B1 protein was compared for identity to the sequences of known genes encoding bacterial transferrin binding proteins, as shown in Table 1.

TABLE 1

| Bacteria | % identity |
| --- | --- |
| Actinobacillus pleuropneumoniae | 49.8% |
| Neisseria meningitidis | 40.4% |
| Neisseria gonorrhoeae | 46.3% |
| Haemophilus influenzae | 48.6% |

The amino acid sequence of the B1 protein (SEQ ID NO:2) was compared for identity and similarity to known bacterial transferrin binding proteins, as shown in Table 2.

TABLE 2

| Bacteria | % similarity | % identity |
| --- | --- | --- |
| Actinobacillus pleuropneumoniae | 44.1% | 38.3% |
| Neisseria meningitidis | 42.8% | 35.4% |
| Neisseria gonorrhoeae | 40.0% | 32.8% |
| Haemophilus influenzae | 38.1% | 32.6% |

Transferrin binding domains of the bacteria listed in Table 1 have been identified by homology with the transferrin binding domains of the TfbA proteins of *A. pleuropneumoniae* (serotype 1, serotype 5, and serotype 7; Strutzberg et al., 1995, *Infect. Immun.* 63:3846–50). Using this technique, at least one of the transferrin binding domains of the B1 protein appears to be located between amino acids 252 to 266 of SEQ ID NO:2. A solid phase transferrin binding assay was used to determine if the clone 6A7 (bacterial lysate) exhibits transferrin-binding activity. The positive control was a whole bacterial lysate from *M. catarrhalis* strain FM2 grown under iron depleted conditions with desferoxamine, and the negative control was a bacterial lysate of the *E. coli* host strain transfected with the plasmid vector lacking the insert. Briefly, an approximately equal amount of each lysate was dotted onto a nitrocellulose membrane. The unbound areas of the nitrocellulose were then blocked with a blocking solution, and then washed. A solution of biotinylated transferrin was added to, and incubated with, the nitrocellulose membrane Following the incubation, the nitrocellulose was washed, incubated with avidin-peroxidase conjugate, washed again, and developed using calorimetric substrate. The results of this assay showed that the whole bacterial lysate of clone 6A7 exhibited strong transferrin binding activity.

In summary, the gene encoding the B1 protein of *M. catarrhalis* was isolated and purified, and the *E. coli* containing the gene produced B1 protein as evidenced by Western blot analysis; solid phase transferrin binding assays; and by the deduced amino acid sequence, and identification of sequence similarity, identity, and binding domain with other bacterial transferrin binding proteins.

Thus, this embodiment illustrates that nucleotide sequences encoding B1 or portions thereof, can be inserted into various vectors including phage vectors, viral vectors, and plasmids. Successful expression of the B1 protein, or peptides of B1 protein, requires that either the insert comprising the gene or gene fragment which encodes epitopes of B1 protein, or the vector itself, contain the necessary elements for transcription and translation which is compatible with, and recognized by the particular host system used for expression. DNA encoding B1 protein or B1 peptides can be synthesized or isolated and sequenced using the methods known in the art, and primer sequences which can be chosen from SEQ ID NO:1. A variety of host cell systems may engineered to contain a gene or gene fragment which encodes epitopes of B1 protein for expressing B1 protein or B1 peptides. The host cell systems include, but are not limited to, bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the DNA sequence encoding B1 amino acid sequences (i.e., recombinant outer membrane B1 protein or B1 peptide) to increase the expression of the B1 amino acid sequence, provided that the increased expression of the B1 amino acid sequence is compatible with (for example, non-toxic to) the particular host cell system used. Thus and importantly, the DNA sequence can consist of the gene encoding B1 protein, or any segment of the gene which encodes a peptide with functional epitope of the B1 protein and/or with the transferrin binding domain (see, e.g., peptide encoded by SEQ ID NO:3, or nucleotide 64 to nucleotide 2136 of SEQ ID NO:1 encoding the amino acid sequence of the mature B1 protein). Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding B1 amino acid sequences.

Additionally, if B1 protein, or B1 peptides may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or IPTG. A variety of operons such as the trp operon, are under different control mechanisms. The trp operon is induced when tryptophan is absent in the growth media. The PL promoter can be induced by an increase in temperature of host cells containing a temperature sensitive lambda repressor. In this way, greater than 95% of the promoter-directed transcription may be inhibited in uninduced cells. Thus expression of recombinant B1 protein, or B1 peptides, may be controlled by culturing transformed or transfected cells under conditions such that the promoter controlling the expression from the inserted DNA encoding B1 amino acids is not induced, and when the cells reach a suitable density in the growth medium, the promoter can be induced for expression from the inserted DNA.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding B1 amino acids to increase transcriptional efficiency. Specific regulatory sequences may be identified from sequence analysis which may effect the expression from the gene encoding B1 protein. These or other regulatory sites, such as transcription or translation initiation signals, can be used to regulate the expression of the gene encoding B1 protein, or gene fragments thereof. Such regulatory elements may be inserted into DNA sequences encoding B1 amino acids or nearby vector DNA sequences using recombinant DNA methods known in the art for insertion of DNA sequences.

Accordingly, *M. catarrhalis* nucleotide sequences encoding B1 protein or B1 peptides ("B1-specific nucleotide sequences) can be ligated into an expression vector at a specific site in relation to the vector's promoter, control, and regulatory elements so that when the recombinant vector is introduced into the host cell, the *M. catarrhalis* B1-specific nucleotide sequences can be expressed in the host cell. For example, the B1-specific nucleotide sequences containing its own regulatory elements can be ligated into an expression vector in a relation or orientation to the vector promoter, and control elements which will allow for expression of B1 amino acid sequences. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immuno-screening for production of B1-specific epitopes using antisera generated to B1-specific epitopes, and probing the DNA of the host's cells for B1-specific nucleotide sequences using one or more oligonucleotides.

Genetic engineering techniques may also be used to characterize, modify and/or adapt the encoded B1 peptides or B1 protein. For example, site-directed mutagenesis to modify an outer membrane protein fragment in regions outside the protective domains, may be desirable to increase the solubility of the subfragment to allow for easier purification. Further, genetic engineering techniques can be used to generate DNA sequences encoding a portion of the amino acid sequence of OMP B1. For example, from the nucleotide sequence disclosed as SEQ ID NO:1 and the amino acid sequence disclosed in SEQ ID NO:2, it can be determined which restriction enzyme or combination of restriction enzymes may be used to generate sequences encoding B1 peptides. Restriction enzyme selection may be done so as not to destroy the immunopotency of the resultant peptide. Antigenic sites of a protein may vary in size but can consist of from about 7 to about 14 amino acids. Thus, a peptide representing a portion of B1 protein may contain many discrete antigenic sites; therefore, many partial gene sequences could encode antigenic epitopes of B1 protein. Consequently, using SEQ ID NOs:1 & 2 as guides, restriction enzyme combinations may be used to generate B1-specific nucleotide sequences, which when inserted into the appropriate vector, are capable of directing the production of B1-specific amino acid sequences (protein or peptides) comprising different antigenic epitopes.

EXAMPLE 2

The present invention relates to a gene, isolated from *M. catarrhalis*, wherein such gene encodes an transferrin binding protein, OMP B1. With sequence information, like that shown in SEQ ID NOs: 1, 2, and 3, other peptides can be produced which display transferrin binding activity. Variant nucleotide sequences can be natural variants or variants produced by synthetic or mutagenic means for modifying the disclosed nucleotide sequences. Methods for synthetically producing such variant sequences are known to those skilled in the art. In designing such variants, one needs to consider avoiding mutations of sequences that encode the amino acids involved in the transferrin binding domain, and which would negatively affect the resultant transferrin binding activity. In that regard, from sequence analysis, it is noted that at least one of the transferrin binding domains involves amino acids 252 to 266 of SEQ ID NO:2. In one embodiment, the variant sequence may be produced by site-directed mutagenesis using one of the several methods for such mutagenesis which are known to those skilled in the art (see, e.g. U.S. Pat. No. 5,397,705) For example, site directed mutagenesis using oligonucleotides comprises the steps of (i) synthesizing an oligonucleotide with a sequence nearly identical to a sequence found in SEQ ID NO:1 except that the oligonucleotide sequence contains the desired nucleotide substitution (encoding for a mutation in the amino acid sequence); (ii) hybridizing the oligonucleotide primer to a template comprising the nucleotide sequence encoding B1 protein; and extending the oligonucleotide primer using a DNA polymerase. The resultant variant sequence may then be incorporated into an expression vector which is then used to genetically engineer a host cell to recombinantly produce a peptide having transferrin binding activity.

In another embodiment, genetic engineering techniques can be used to generate nucleic acid molecules comprising a variant sequence that is a substantial portion of SEQ ID NO:1. As apparent to one skilled in the art, from the sequence disclosed as SEQ ID NO:1 and from the restriction maps of SEQ ID NO:1 generated using methods standard in the art, it can be determined which restriction enzyme or combination of restriction enzymes may be used to generate nucleic acid molecules (fragments of SEQ ID NO:1; e.g., SEQ ID NO:3, and nucleotide 64 to nucleotide 2136 of SEQ ID NO:1) encoding a peptide having transferrin binding activity. Restriction enzyme selection may be done so as not to destroy the transferrin binding domain. Consequently, using SEQ ID NO:1 as a guide, restriction enzyme combinations may be used to generate nucleic acid molecules (gene fragments), which when inserted into the appropriate vector, are capable of directing the production of peptides having transferrin binding activity.

EXAMPLE 3

This example illustrates methods for using B1-specific nucleotide sequences in molecular diagnostic assays for the detection of *M. catarrhalis*. OMP B1 contains some antigenically conserved epitopes (Sethi et al., 1995, *Infect. Immun.* 63:1516–20), and hence some molecular conservation at the nucleic acid sequence level. Thus, a gene encoding B1 protein, or nucleic acid sequences derived therefrom, of the present invention can be used in molecular diagnostic assays for detecting *M. catarrhalis* genetic material. In particular, and as illustrated by SEQ ID NOs:4–9, B1 sequence-specific oligonucleotides can be synthesized for use as primers and/or probes in amplifying, and detecting amplified, nucleic acids from *M. catarrhalis*. There are several means known in the art for enzymatically amplifying nucleic acid sequences. Currently the most commonly used method, PCR™ (polymerase chain reaction, Perkin Elmer Corporation) involves the use of a thermostable DNA Polymerase, known sequences as primers, and heating cycles which separate the replicating deoxyribonucleic acid (DNA) strands and exponentially amplify a gene of interest. Other amplification methods include LCR™ (ligase chain reaction) which utilizes DNA ligase, and a probe consisting of two halves of a DNA segment that is complementary to the sequence of the DNA to be amplified; enzyme QB replicase and a ribonucleic acid (RNA) sequence template attached to a probe complementary to the DNA to be copied which is used to make a DNA template for exponential production of complementary RNA; and NASBA™ (nucleic acid sequence-based amplification) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$–$10^4$ organisms per specimen (1990, *Gene Probes for Bacteria*, eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the gene encoding B1 protein of *M. catarrhalis*, and to probes which specifically hybridize with these amplified DNA fragments. By using the nucleic acid sequences of the present invention, and according to the methods of the present invention, as few as one *M. catarrhalis* organism may be detected in the presence of 10 µg/ml extraneous DNA.

This embodiment is directed to species-specific oligonucleotides which can be used to amplify sequences of *M. catarrhalis* DNA, if present, from DNA extracted from clinical specimens including middle ear fluid, sputum, blood, and fluids from the nasopharynx, eye, and adenoid; and to subsequently determine if amplification has occurred. In one embodiment of the present invention, a pair of *M. catarrhalis*-specific DNA oligonucleotide primers are used to hybridize to *M. catarrhalis* genomic DNA that may be present in DNA extracted from a clinical specimen, and to amplify the specific segment of genomic DNA between the two flanking primers using enzymatic synthesis and temperature cycling. Each pair of primers are designed to hybridize only to the *M. catarrhalis* nucleotide sequences comprising the gene encoding OMP B1 (i.e. within the region of the genome containing SEQ ID NO:1) to which they have been synthesized to complement; one to each strand of the double-stranded DNA. Thus, the reaction is specific even in the presence of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the *M. catarrhalis* DNA sequences, if present, results. Further identification of the amplified DNA fragment, as being derived from *M. catarrhalis* DNA, may be accomplished by liquid hybridization. This test utilizes one or more labeled oligonucleotides as probes to specifically hybridize to the amplified segment of *M. catarrhalis* DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of *M. catarrhalis*. In a related embodiment, the oligonucleotides used as primers may be labeled directly, or synthesized to incorporate label. Depending on the label used, the amplification products can then be detected, after binding onto an affinity matrix, using isotopic or calorimetric detection.

DNA may be extracted from clinical specimens which may contain *M. catarrhalis* using methods known in the art. For example, cells contained in the specimen may be washed in TE buffer and pelleted by centrifugation. The cells then may be resuspended in 100 $\mu$l of amplification reaction buffer containing detergents and proteinase K. Using the polymerase chain reaction, the resultant sample may be composed of the cells in 10 mM Tris pH 8.3, 50 mM KCl, 15 mM MgCl$_2$, 0.01% gelatin, 0.45% NP40™, 0.045% Tween 20™, and 60 $\mu$g/ml proteinase K. The sample is incubated at 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The *M. catarrhalis* DNA may be amplified using any one of several protocols for amplifying nucleic acids by the polymerase chain reaction. In one mode of this embodiment, the gene encoding B1 protein may be amplified from a clinical isolate of *M. catarrhalis* using the following conditions. DNA to be amplified ($\approx$1 $\mu$g of genomic DNA) is distributed in 0.5 ml microfuge tubes and the volume is adjusted to 50 $\mu$l by adding a reaction mixture comprising 0.2 mM dNTPs (dATP, dCTP, dGTP, dTTP), 0.25 $\mu$g of each positive and negative oligonucleotide primer, 1 unit of thermostable DNA polymerase, polymerase 10× buffer (5 $\mu$l), 3 mM MgSO$_4$ (final concentration), and sterile distilled water to achieve the total volume. The DNA polymerase is added to the reaction mixture just before use and is gently mixed, not vortexed. A layer of mineral oil, approximately 2 drops, is added to each tube and then the tubes are placed in the thermal cycler. Thirty to thirty-five cycles are generally sufficient for bacterial DNA amplification. One cycle consists of 15 seconds at 96° C., 1 minute at 62° C., and 1 minute at 74° C. The first cycle includes a 3 minute incubation at 95° C. to assure complete denaturation.

Oligonucleotides useful as primers or probes which specifically hybridize to the gene encoding B1 protein of *M. catarrhalis* and used in DNA amplification and/or detection can be biochemically synthesized, using methods known in the art, from the nucleotide sequences disclosed in the present invention. The specificity of the oligonucleotides for *M. catarrhalis* can be checked by a gene-bank database (Genbank) search for each individual sequence. In general, the oligonucleotides should be selected for low G-C content. Lengths for primers and probes may vary, but typically may be from approximately 10 bp to approximately 40 bp in length. Illustrative pairs of primers used to amplify portions of the gene encoding B1 protein include SEQ ID NOs:4 and 5; SEQ ID NOs:6 and 7; and SEQ ID NOs:8 and 9.

For detection purposes, the oligonucleotides of the present invention may be end-labeled with a radioisotope. Probe sequences, internal to the two primers used for amplification of the gene sequence, may be end-labeled using T$_4$ polynucleotide kinase and gamma $^{32}$P ATP. Twenty pMols of probe DNA in kinase buffer (50 mM Tris, pH 7.6, 10 mM MgCl$_2$, 5 mM dithiothreitol, 0.1 mM spermidine-HCl, 0.1 mM EDTA, pH 8.0) is mixed with 120 $\mu$Ci of gamma $^{32}$P ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fiber filter, by liquid scintillation. Such probe sequences may be a sequence chosen from SEQ ID NO:1 provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternately, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

EXAMPLE 4

This example illustrates methods for using B1-specific nucleotide sequences or variant sequences for producing recombinant B1 protein, or peptides thereof. In one illustration of this embodiment, recombinant B1 protein or B1 peptide may be purified from a polyhistidine expression plasmid. To purify recombinant B1 protein by this method, the gene encoding B1 protein is amplified with primers corresponding to the 5' and 3' ends of the gene, wherein the primers are designed to include EcoRI and BamHI restriction sites. The resulting DNA fragment is then cloned into a commercially available polyhistidine expression vector such as plasmid pRSETA (which is restricted with EcoRI and BanHI) (Invitrogen), such that upon expression several histidine residues ("polyhistidine tail") are attached to the amino terminus of the B1 protein. The ligation mixture is used to electroporate $E.$ $coli$ host strain (BLR(DE3)) cells, and transformants are analyzed for recombinant plasmids containing the gene encoding B1 protein in the proper orientation with respect to the plasmid promoter.

Recombinant B1 protein may then be purified as follows. A single colony of a clone containing the gene encoding B1 protein is inoculated into broth media containing 200 $\mu$g/ml carbenicillin. The culture is incubated at 37° C. until the cells were in log phase of growth. The cells are then harvested and resuspended in 2 ml of fresh broth; and a 0.1 ml aliquot is used to inoculate an 8 ml culture containing 500 $\mu$g/ml carbenicillin. The 8 ml culture is incubated at 37° C. until the cells are in log phase of growth. The cells are then harvested and resuspended in 50 ml of fresh broth containing 500 $\mu$g/ml carbenicillin and 1 mM IPTG. After incubating at 30° C. for 2 hours, the cells are harvested by centrifugation at 6,000×g for 10 minutes at 4° C. The harvested cells are resuspended in 5 ml of guanidinium lysis buffer (6 M guanidine hydroxide, 50 mM sodium phosphate, 100 mM sodium chloride, 10 mM Tris pH 8.0). The suspension is mixed for 20 minutes at room temperature The mixture is then centrifuged at 10,000×g for 10 minutes at 4° C. and the supernatant (the bacterial lysate) is saved.

The supernatant is then mixed for 10 minutes at room temperature with a resin (e.g., Talon™ resin; 1 ml of resin per 75 ml of culture) which, via a metal on the resin, binds to the polyhistidine taxi of the recombinant B1 protein. The resin is then isolated by centrifugation. The resin is washed with 10 volumes of guanidinium lysis buffer for 10 minutes at room temperature. The resin is then centrifuged, and the wash repeated. An additional wash is performed using 10 volumes of a buffer ("TON buffer" comprising 20 mM Tris pH 8.0, 1% β-octylglucoside, 500 mM NaCl) for 10 minutes at room temperature, and then the resin is collected by centrifugation. The B1 protein is eluted from the resin with two volumes of TON buffer containing 50 mM EDTA with agitation for 10 minutes at room temperature. The resin is then pelleted by centrifugation, and the supernatant containing B1 protein is saved.

EXAMPLE 5

This example illustrates using B1-specific nucleotide sequences or variant sequences in antigenic compositions for inducing anti-B1 antibodies in an immunized individual. In one embodiment, provided is either a live recombinant viral vaccine, recombinant bacterial vaccine, recombinant attenuated bacterial vaccine, or an inactivated recombinant viral vaccine which is used to protect against infections caused by $M.$ $catarrhalis$. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as B1 protein, or B1 peptides, thereby providing long-lasting immunity. Other live vaccine vectors include: adenovirus, cytomegalovirus, and preferably the poxviruses such as vaccinia (Paoletti and Panicali, U.S. Pat. No. 4,603, 112) and attenuated Salmonella strains (Stocker et al., U.S. Pat. Nos. 5,210,035; 4,837,151; and 4,735,801; and Curtiss et al., 1988, $Vaccine$ 6:155–160). Live vaccines are particularly advantageous because they continually stimulate the immune system which can confer substantially long-lasting immunity. When the immune response is protective against subsequent $M.$ $catarrhalis$ infection, the live vaccine itself may be used in a preventative vaccine against $M.$ $catarrhalis$.

To illustrate this mode of the embodiment, using molecular biological techniques such as those illustrated in Example 1, the gene encoding B (SEQ ID NO:1), or a gene fragment encoding a peptide derived therefrom (e.g., SEQ ID NO:3), or a variant sequence, may be inserted into the vaccinia virus genomic DNA at a site which allows for expression of B1-specific epitopes but does not negatively affect the growth or replication of the vaccinia virus vector. The resultant recombinant virus can be used as the immunogen in an antigenic formulation comprising a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. A mixture of inactivated viruses which express different epitopes may be used in the formulation of a multi-valent inactivated vaccine. In either case, the inactivated recombinant vaccine or mixture of inactivated viruses may be formulated with a suitable adjuvant in order to enhance the immunological response to the vaccine antigens.

In another variation of this embodiment, genetic material is used directly as the vaccine formulation. B1-specific nucleotide sequences (or variant sequences) encoding B1 protein or encoding a B1 peptide, and operatively linked to one or more regulatory elements can be introduced directly to vaccinate the individual ("direct gene transfer") against pathogenic strains of *M. catarrhalis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, *Science* 261:209–211). Additionally, the recombinant DNA may further comprise one or more immuno-stimulatory DNA sequences known to be necessary for optimal immunization (Sato et al., 1996, *Science* 273:352). Other effective methods for delivering vector DNA into a target cell are known in the art. In one example, purified recombinant plasmid DNA containing viral genes has been used to inoculate (whether parentally, mucosally, or via gene-gun immunization) vaccinees to induce a protective immune response (Fynan et al., 1993, *Proc. Natl. Acad. Sci. USA* 90:11478–11482). In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express B1 protein, or B1 peptide.

One preferred method of vaccination with genetic material comprises the step of administering to the individual a therapeutically effective amount of an antigenic composition comprising a nucleic acid molecule that comprises a B1-specific nucleotide sequence (or variant sequence) encoding B1 protein, or B1 peptides, or a combination thereof, wherein the nucleic acid molecule is operatively linked to one or more regulatory sequences necessary for expression. The nucleic acid molecule can be administered directly, or first introduced into a viral vector and administered via the vector. The nucleic acid molecule can be administered in a pharmaceutically acceptable carrier or diluent and may contain compounds that can enhance the effectiveness of the vaccine. These additional compounds include, but are not limited to, adjuvants that modulate and enhance the immune response, or other compounds which increase the uptake of nucleic acid by the cells. The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

It should be understood that while the invention has been described in detail herein, the examples were for illustrative purposes only. Other modifications of the embodiments of the present invention that are obvious to those skilled in the art of microbial pathogenesis, medical diagnostics, vaccines, and related disciplines are intended to be within the scope of the appended claims.

We claim:

1. A recombinant vector comprising a nucleotide sequence encoding one or more antigenic epitopes of B1 protein, wherein B1 protein is an outer membrane protein of *Moraxella catarrhalis* having an apparent molecular mass determined by polyacrylamide gel electrophoresis of about 81,000 about to 84,000 daltons wherein said B1 protein comprises an amino acid sequence shown in SEQ ID NO:2.

2. The recombinant vector according to claim 1, wherein B1 protein comprises an amino acid sequence of amino acid residue 22 to amino acid residue 712 of SEQ ID NO:2.

3. The recombinant vector according to claim 1, wherein the vector is selected from the group consisting of a plasmid vector, phagemid vector, cosmid vector, and a viral vector.

4. An isolated nucleic acid segment selected from the group consisting of a gene depicted in SEQ ID NO:1, and a fragment of said gene, wherein said fragment encodes at least one epitope of B1 protein, wherein B1 protein is an outer membrane protein of *Moraxella catarrhalis* having an apparent molecular mass of about 81,000 about to 84,000 daltons determined by polyacrylamide gel electrophoresis wherein said B1 protein comprises an amino acid sequence shown in SEQ ID NO:2.

5. An isolated and purified nucleic acid segment consisting of a gene encoding B1 protein, wherein B1 protein is an outer membrane protein of *Moraxella catarrhalis* having an apparent molecular mass determined by polyacrylamide gel electrophoresis of about 81,000 about to 84,000 daltons wherein said B1 protein comprises an amino acid sequence shown in SEQ ID NO:2.

6. The nucleic acid segment according to claim 5, wherein the gene has a nucleotide sequence depicted in SEQ ID NO:1.

7. A recombinant virus or recombinant microorganism containing the recombinant vector of claim 1, and expressing a B1 amino acid sequence selected from the group consisting of B1 protein, and an antigenic epitope of B1 protein.

8. A virus of claim 7, which is a vaccinia virus, adenovirus, or cytomegalovirus.

9. A microorganism of claim 7, which is a bacterium of the genus Salmonella, or the genus Escherichia.

10. A recombinant virus or recombinant microorganism containing the nucleic acid segment of claim 4, and expressing a B1 amino acid sequence selected from the group consisting of B1 protein, and an antigenic epitope of B1 protein.

11. A virus of claim 10, which is a vaccinia virus, adenovirus, or cytomegalovirus.

12. A microorganism of claim 10, which is a bacterium of the genus Salmonella, or the genus Escherichia.

13. A recombinant microorganism containing the nucleic acid segment of claim 5, and expressing B1 protein.

14. A method for producing a purified peptide or protein having one or more antigenic epitopes of B1 protein, wherein B1 protein is an outer membrane protein of *Moraxella catarrhalis* comprising amino acid sequence SEQ ID NO:2, said method comprises (a) growing in culture a host cell system containing the nucleic acid segment of claim 4 for expression; and (b) isolating said peptide or protein having one or more antigenic epitopes of B1 protein expressed from the cultured host cell system or from medium used for culture.

15. The method according to claim 14, wherein the host cell system is a host cell selected from the group consisting of a recombinant microorganism, yeast, fungi, insect cell lines, and mammalian cell lines.

16. A method for producing a purified peptide or protein having one or more antigenic epitopes of B1 protein, wherein B1 protein is an outer membrane protein of *Moraxella catarrhalis* comprising amino acid sequence SEQ ID NO:2, said method comprises (a) growing in culture a host cell system containing the nucleic acid segment of claim 5 for expression; and (b) isolating the B1 protein expressed from the cultured host cell system or from medium used for culture.

17. The method according to claim 16, wherein the host cell system is a host cell selected from the group consisting of a recombinant microorganism, yeast, fungi, insect cell lines, and mammalian cell lines.

18. An isolated nucleic acid segment selected from the group consisting of SEC ID NO:1, SEQ ID NO:2, SEQ ID NO:3, SEQ ID NO:5, SEQ ID NO:6, SEQ ID NO:7, SEQ ID NO:8, and SEQ ID NO:9.

* * * * *

UNITED STATES PATENT AND TRADEMARK OFFICE
CERTIFICATE OF CORRECTION

PATENT NO. : 5,972,657
DATED : October 26, 1999
INVENTOR(S) : Murphy et al.

It is certified that error appears in the above-identified patent and that said Letters Patent is hereby corrected as shown below:

Col. 29, line 14 - delete "about to" and insert --to about--.

Col. 29, line 27 - delete "about to" and insert --to about--.

Col. 29, line 35 - delete "about to" and insert --to about--.

Signed and Sealed this

Sixteenth Day of May, 2000

Attest:

Q. TODD DICKINSON

*Attesting Officer*   *Director of Patents and Trademarks*

SEQUENCE LISTING (1) GENERAL INFORMATION:

(iii) NUMBER OF SEQUENCES: 9

(2) INFORMATION FOR SEQ ID NO: 1 :

(i) SEQUENCE CHARACTERISTICS:
      (A) LENGTH: 2136 nucleotides
      (B) TYPE: nucleic acid
      (C) STRANDEDNESS: double-stranded
      (D) TOPOLOGY: linear (ii) MOLECULE TYPE: genomic DNA (iii) HYPOTHETICAL: yes (vi) ORIGINAL SOURCE:
      (A) ORGANISM: Moraxella catarrhalis
      (B) STRAIN: FM2
      (G) CELL TYPE: bacterium (vii) IMMEDIATE SOURCE:
      (A) LIBRARY: genomic
      (B) CLONE: lambda clone (xi) SEQUENCE DESCRIPTION: SEQ ID NO:1:

```
ATG AAA CAC ATT CCT TTA ACC ACA CTG TGT GTG GCA ATC TCT GCC            45

GTC TTA TTA ACC GCT TGT GGT GGC AGT GGT GGT TCA AAT CCA CCT            90

GCT CCT ACG CCC ATT CCA AAT GCT AGC GGT TCA GGT AAT ACT GGC           135

AAC ACT GGT AAT GCT GGC GGT ACT GAT AAT ACA GCC AAT GCA GGT           180
```

-continued

| | |
|---|---|
| AAT ACA GGC GGT ACA AGC TCT GGT ACA GGC AGT GCC AGC ACG TCA | 225 |
| GAA CCA AAA TAT CAA GAT GTG CCA ACA ACG CCC AAT AAC AAA GAA | 270 |
| CAA GTT TCA TCC ATT CAA GAA CCT GCC ATG GGT TAT GCA ATG GAA | 315 |
| TTA AAG CTT CGT AAT GCT CAC CCT CAT AAC CCA AAT AAA GAA ACC | 360 |
| GAA AAA CGC ATC GCC TTA GAC CAA AAA GAT TTG GTG GCG GTA GAG | 405 |
| GGC AAT CTA ACC AAT ATT CCT TTT GAT AAA AAT CTT ATT GAA TAC | 450 |
| CTT AAA AAA TCA CCC GAG GTT GTA AGT AAA TTC AAT GAA CAA AAA | 495 |
| GGC GGT ATT GAA AAT AAC ACA AGA TTG ACA CAC AAA GAT TTA TCA | 540 |
| TCA GAG CAA AAA GAA GCA AAA GTC AAA GAA GCG TTG GAC AAT GCT | 585 |
| TTA ACT CAA TTT GCC CAA GAA AAA TAC AAG GAG CTA ATT GAG AAC | 630 |
| GCC CAT GAT AAA AAA TCT GAT GCA CGC AAC CGT GAC CTA AAA TAT | 675 |
| GTC AAG TCT GGT TTT AAC TAT CTT TCT GGA TAT ACC GCC ACC GAC | 720 |
| CAC GAC AAA AAA ACC AAT TAT CGT GGC TAT TAT GGT GCG TTG TAT | 765 |
| TAT AAA GGA AGC GAA ACC GCC AAA GAG TTG CCA CAA ACA AGT GCA | 810 |
| AAA TAT AAA GGT TAT TGG GAC TTT ATG ACA GAT GCC ACA CTT GAT | 855 |
| AAC AAA TAC ACG GAT TTG CCA GGT ATC GCC AGA CAA ACC CAG TGG | 900 |
| CGT AGT CTT GTT TCT ACT GAT GAG TAT GCA ACG CTC TTG ACA GAC | 945 |
| AAA AAT AAT AAG CCT AGT GAT TAC AAT GGT GCA TAT GGT CAT AGC | 990 |
| AGT GAA TTT GAT GTT AAT TTT GCT GAC AAA AAA GTC ACA GGT AAA | 1035 |
| CTT ATC AGT AAT CAG TTA TCA GGC AAA ACT GTA ACC GCT AAA GAG | 1080 |
| CGT TAT AAA ATA GAA GCT GAT ATC CAC GGC AAC CGC TTC CGT GGC | 1125 |
| AGT GCC ATC GCA AGC GAA AAA ACA GAT GAA AGC AAA AGC AAA CAT | 1170 |
| CCC TTT ACC AGT GAT GCC AAA GAT AGG CTA GAA GGC GGT TTT TAT | 1215 |
| GGG CCA AAA GGC GAG GAG CTG GCA GGT AAA TTC TTA ACC GAT GAC | 1260 |
| AAC AAA CTC TTT GGT GTC TTT GGT GCT AAA CGA GAG AGT AAA GCT | 1305 |
| GGG GAA AAA ACC GAA GCC ATC TTA GAT GCC TAT GCA CTT GGG ACA | 1350 |
| TTT AAT AAA TCT GGT ACG ACC AAC CCC GCC TTT AAC GCT AAC AGT | 1395 |
| AAA AAA GAA CTG GAT AAT TTT GGC AAT ATT AAT AAA TTG GTC TTG | 1440 |
| GGT TCT ACT GTG ATA GAC CTT ACT CAA GGT AAT GAT TTT GTA AAA | 1485 |
| ACC ATT GAT AAA GAA AAA CCA GCC ACC ACC AGC AAT CAA GCA GGA | 1530 |
| GAG CCT TTG ACG GTG AAT GAT AAG GTT CAG GTA CAA GTT TGT TGT | 1575 |
| AGC AAT CTT GAG CAT CTA AAA TTT GGT TCA CTG AGT ATC GGT GAT | 1620 |
| AGT AAT AGC GTA TTT TTA CAA GGT GAA CGC ACC GCC ACC ACA GGT | 1665 |
| GAT AAA GCC ATG CCA GTT GTA GGA AAT GCT AAA TAT CGT GGT ACA | 1710 |
| TGG GCA GGC TAT GTT ACA GGC TCT GGT AAT ACC AGC AAA GGC TAT | 1755 |
| GAA GCT CAA AAA TTT GCT GAT AAT GCC AAC CGT GCC GAG TTT GAT | 1800 |
| GTA GAC TTT GCT AAA AAA AGT CTA ACT GGT AAG CTT ATT CCA AAT | 1845 |
| ACG AGC AGT GAT GGT AAA TCT GCT TTT GAT ATT ACC GCT ACG ATT | 1890 |
| GAT GGC AAT GGT TTT AGT GGT AAA GCC AAT ACA CCA GAC ATT AAA | 1935 |
| ACA GGT GGG TTA AAG ATT GAC AGT AAG AAC ACT GAA AGC GGT CGA | 1980 |

```
GTA ATT GTG AAA GAT GCT GTA GTT ACA GGT GGC TTT TAT GGT CCA         2025

CAA GCT AAT GAA CTT GGT GGC TCA TTT ACC TAC AAG AGC AAT GAT         2070

GCT GAA AAC AAA GAC AGT AGT GCA TCT GTG GTC TTT GGT GCA AGA         2115

AAA CAA CAA GAA GTT AAG CAG                                         2136
```

(2) INFORMATION FOR SEQ ID NO:2:

(i) SEQUENCE CHARACTERISTICS:
        (A) LENGTH: 707 residues
        (B) TYPE: amino acid
        (C) TOPOLOGY: linear (ii) MOLECULE TYPE:
        (A) DESCRIPTION: protein (iii) HYPOTHETICAL: yes (xi) SEQUENCE DESCRIPTION: SEQ ID NO:2:

```
Met Lys His Ile Pro Leu Thr Thr Leu Cys Val Ala Ile Ser Ala
 1               5                  10                  15

Val Leu Leu Thr Ala Cys Gly Gly Ser Gly Gly Ser Asn Pro Pro
                20                  25                  30

Ala Pro Thr Pro Ile Pro Asn Ala Ser Gly Ser Gly Asn Thr Gly
                35                  40                  45

Asn Thr Gly Asn Ala Gly Gly Thr Asp Asn Thr Ala Asn Ala Gly
                50                  55                  60

Asn Thr Gly Gly Thr Ser Ser Gly Thr Gly Ser Ala Ser Thr Ser
                65                  70                  75

Glu Pro Lys Tyr Gln Asp Val Pro Thr Thr Pro Asn Asn Lys Glu
                80                  85                  90

Gln Val Ser Ser Ile Gln Glu Pro Ala Met Gly Tyr Ala Met Glu
                95                 100                 105

Leu Lys Leu Arg Asn Ala His Pro His Asn Pro Asn Lys Glu Thr
               110                 115                 120

Glu Lys Arg Ile Ala Leu Asp Gln Lys Asp Leu Val Ala Val Glu
               125                 130                 135

Gly Asn Leu Thr Asn Ile Pro Phe Asp Lys Asn Leu Ile Glu Tyr
               140                 145                 150

Leu Lys Lys Ser Pro Glu Val Val Ser Lys Phe Asn Glu Gln Lys
               155                 160                 165

Gly Gly Ile Glu Asn Asn Thr Arg Leu Thr His Lys Asp Leu Ser
               170                 175                 180

Ser Glu Gln Lys Glu Ala Lys Val Lys Glu Ala Leu Asp Asn Ala
               185                 190                 195

Gln Glu Lys Tyr Lys Glu Leu Ile Glu Asn Ala His Asp Lys Lys
               200                 205                 210

Ser Asp Ala Arg Asn Arg Asp Leu Lys Tyr Val Lys Ser Gly Phe
               215                 220                 225

Asn Tyr Leu Ser Gly Tyr Thr Ala Thr Asp His Asp Lys Lys Thr
               230                 235                 240

Asn Tyr Arg Gly Tyr Tyr Gly Ala Leu Tyr Tyr Lys Gly Ser Glu
               245                 250                 255

Thr Ala Lys Glu Leu Pro Gln Thr Ser Ala Lys Tyr Lys Gly Tyr
               260                 265                 270

Trp Asp Phe Met Thr Asp Ala Thr Leu Asp Asn Lys Tyr Thr Asp
               275                 280                 285
```

```
Leu Pro Gly Ile Ala Arg Gln Thr Gln Trp Arg Ser Leu Val Ser
            290                 395                 300

Thr Asp Glu Tyr Ala Thr Leu Leu Thr Asp Lys Asn Asn Lys Pro
            305                 310                 315

Ser Asp Tyr Asn Gly Ala Tyr Gly His Ser Ser Glu Phe Asp Val
            320                 325                 330

Asn Phe Ala Asp Lys Lys Val Thr Gly Lys Leu Ile Ser Asn Gln
            335                 340                 345

Leu Ser Gly Lys Thr Val Thr Ala Lys Glu Arg Tyr Lys Ile Glu
            350                 355                 360

Ala Asp Ile His Gly Asn Arg Phe Arg Gly Ser Ala Ile Ala Ser
            365                 370                 375

Glu Lys Thr Asp Glu Ser Lys Ser Lys His Pro Phe Thr Ser Asp
            380                 385                 390

Ala Lys Asp Arg Leu Glu Gly Gly Phe Tyr Gly Pro Lys Gly Glu
            395                 400                 405

Glu Leu Ala Gly Lys Phe Leu Thr Asp Asp Asn Lys Leu Phe Gly
            410                 415                 420

Val Phe Gly Ala Lys Arg Glu Ser Lys Ala Gly Glu Lys Thr Glu
            425                 430                 435

Ala Ile Leu Asp Ala Tyr Ala Leu Gly Thr Phe Asn Lys Ser Gly
            440                 445                 450

Thr Thr Asn Pro Ala Phe Asn Ala Asn Ser Lys Lys Glu Leu Asp
            455                 460                 465

Asn Phe Gly Asn Ile Asn Lys Leu Val Leu Gly Ser Thr Val Ile
            470                 475                 480

Asp Leu Thr Gln Gly Asn Asp Phe Val Lys Thr Ile Asp Lys Glu
            485                 490                 495

Lys Pro Ala Thr Thr Ser Asn Gln Ala Gly Glu Pro Leu Thr Val
            500                 505                 510

Asn Asp Lys Val Gln Val Gln Val Cys Cys Ser Asn Leu Glu His
            515                 520                 525

Leu Lys Phe Gly Ser Leu Ser Ile Gly Asp Ser Asn Ser Val Phe
            530                 535                 540

Leu Gln Gly Glu Arg Thr Ala Thr Thr Gly Asp Lys Ala Met Pro
            545                 550                 555

Val Val Gly Asn Ala Lys Tyr Arg Gly Thr Trp Ala Gly Tyr Val
            560                 565                 570

Thr Gly Ser Gly Asn Thr Ser Lys Gly Tyr Glu Ala Gln Lys Phe
            575                 580                 585

Ala Asp Asn Ala Asn Arg Ala Glu Phe Asp Val Asp Phe Ala Lys
            590                 595                 600

Lys Ser Leu Thr Gly Lys Leu Ile Pro Asn Thr Ser Ser Asp Gly
            605                 610                 615

Lys Ser Ala Phe Asp Ile Thr Ala Thr Ile Asp Gly Asn Gly Phe
            620                 625                 630

Ser Gly Lys Ala Asn Thr Pro Asp Ile Lys Thr Gly Gly Leu Lys
            635                 640                 645

Ile Asp Ser Lys Asn Thr Glu Ser Gly Arg Val Ile Val Lys Asp
            650                 655                 660

Ala Val Val Thr Gly Gly Phe Tyr Gly Pro Gln Ala Asn Glu Leu
            665                 670                 675

Gly Gly Ser Phe Thr Tyr Lys Ser Asn Asp Ala Glu Asn Lys Asp
```

```
                    680             685             690
Ser Ser Ala Ser Val Val Phe Gly Ala Arg Lys Gln Gln Glu Val
                        695             700             705

Lys Gln
    707
```

(2) INFORMATION FOR SEQ ID NO:3 :

(i) SEQUENCE CHARACTERISTICS:
        (A) LENGTH: 900 Nucleotides
        (B) TYPE: nucleic acid
        (C) STRANDEDNESS: double-stranded
        (D) TOPOLOGY: linear (ii) MOLECULE TYPE: DNA (iii) HYPOTHETICAL: No (xi) SEQUENCE DESCRIPTION: SEQ ID NO:3 :

```
ATG AAA CAC ATT CCT TTA ACC ACA CTG TGT GTG GCA ATC TCT GCC        45
GTC TTA TTA ACC GCT TGT GGT GGC AGT GGT GGT TCA AAT CCA CCT        90
GCT CCT ACG CCC ATT CCA AAT GCT AGC GGT TCA GGT AAT ACT GGC       135
AAC ACT GGT AAT GCT GGC GGT ACT GAT AAT ACA GCC AAT GCA GGT       180
AAT ACA GGC GGT ACA AGC TCT GGT ACA GGC AGT GCC AGC ACG TCA       225
GAA CCA AAA TAT CAA GAT GTG CCA ACA ACG CCC AAT AAC AAA GAA       270
CAA GTT TCA TCC ATT CAA GAA CCT GCC ATG GGT TAT GCA ATG GAA       315
TTA AAG CTT CGT AAT GCT CAC CCT CAT AAC CCA AAT AAA GAA ACC       360
GAA AAA CGC ATC GCC TTA GAC CAA AAA GAT TTG GTG GCG GTA GAG       405
GGC AAT CTA ACC AAT ATT CCT TTT GAT AAA AAT CTT ATT GAA TAC       450
CTT AAA AAA TCA CCC GAG GTT GTA AGT AAA TTC AAT GAA CAA AAA       495
GGC GGT ATT GAA AAT AAC ACA AGA TTG ACA CAC AAA GAT TTA TCA       540
TCA GAG CAA AAA GAA GCA AAA GTC AAA GAA GCG TTG GAC AAT GCT       585
TTA ACT CAA TTT GCC CAA GAA AAA TAC AAG GAG CTA ATT GAG AAC       630
GCC CAT GAT AAA AAA TCT GAT GCA CGC AAC CGT GAC CTA AAA TAT       675
GTC AAG TCT GGT TTT AAC TAT CTT TCT GGA TAT ACC GCC ACC GAC       720
CAC GAC AAA AAA ACC AAT TAT CGT GGC TAT TAT GGT GCG TTG TAT       765
TAT AAA GGA AGC GAA ACC GCC AAA GAG TTG CCA CAA ACA AGT GCA       810
AAA TAT AAA GGT TAT TGG GAC TTT ATG ACA GAT GCC ACA CTT GAT       855
AAC AAA TAC ACG GAT TTG CCA GGT ATC GCC AGA CAA ACC CAG TGG       900
```

(2) INFORMATION FOR SEQ ID NO:4 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (xi) SEQUENCE DESCRIPTION: SEQ ID NO:4 :

```
GCGGTTCAGG TAATACTG                                                18
```

(2) INFORMATION FOR SEQ ID NO:5 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (xi) SEQUENCE DESCRIPTION: SEQ ID NO:5 :

CCTGTTTTAA TGTCTGGT                                                 18

(2) INFORMATION FOR SEQ ID NO:6 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (xi) SEQUENCE DESCRIPTION: SEQ ID NO:6 :

AATCACCCGA GGTTGTAA                                                 18

(2) INFORMATION FOR SEQ ID NO:7 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (xi) SEQUENCE DESCRIPTION: SEQ ID NO:7 :

GCTTCATAGC CTTTGCTG                                                 18

(2) INFORMATION FOR SEQ ID NO:8 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No (xi) SEQUENCE DESCRIPTION: SEQ ID NO:8 :

TTCTGGATAT ACCGCCAC                                                 18

(2) INFORMATION FOR SEQ ID NO:9 :

(i) SEQUENCE CHARACTERISTICS:
        (A) LENGTH: 18 nucleotides
        (B) TYPE: nucleic acid
        (C) STRANDEDNESS: single-stranded
        (D) TOPOLOGY: linear (ii) MOLECULE TYPE: DNA (iii) HYPOTHETICAL: No -continued (xi) SEQUENCE DESCRIPTION: SEQ ID NO:9 :

GAACCTTATC ATTCACCG                                                                                              18